(12) United States Patent
Tsuru et al.

(10) Patent No.: US 8,257,445 B2
(45) Date of Patent: Sep. 4, 2012

(54) BONE-COMPATIBLE IMPLANT AND METHOD OF PRODUCING THE SAME

(75) Inventors: Kanji Tsuru, Fukuoka (JP); Satoshi Hayakawa, Soja (JP); Akiyoshi Osaka, Okayama (JP); Atsushi Sugino, Okayama (JP); Kenji Doi, Okayama (JP); Koichi Kuramoto, Okayama (JP)

(73) Assignee: Nakashima Medical Co., Ltd., Okayama (JP)

( * ) Notice: Subject to any disclaimer, the term of this patent is extended or adjusted under 35 U.S.C. 154(b) by 1120 days.

(21) Appl. No.: 12/096,963

(22) PCT Filed: Dec. 7, 2006

(86) PCT No.: PCT/JP2006/324470
§ 371 (c)(1),
(2), (4) Date: Jun. 11, 2008

(87) PCT Pub. No.: WO2007/069532
PCT Pub. Date: Jun. 21, 2007

(65) Prior Publication Data
US 2009/0130632 A1    May 21, 2009

(30) Foreign Application Priority Data

Dec. 12, 2005  (JP) ................................ 2005-357213

(51) Int. Cl.
*A61C 13/08* (2006.01)
*A61F 2/28* (2006.01)
(52) U.S. Cl. ................... 623/23.53; 433/201.1; 604/175
(58) Field of Classification Search ............... 433/201.1; 604/175; 623/23.53
See application file for complete search history.

(56) References Cited

U.S. PATENT DOCUMENTS

| | | |
|---|---|---|
| 5,849,417 A | 12/1998 | Sawada et al. |
| 2003/0125808 A1 | 7/2003 | Hunter et al. |
| 2003/0157349 A1 | 8/2003 | Kasuga et al. |
| 2005/0234558 A1 | 10/2005 | Petersson et al. |
| 2006/0122708 A1 | 6/2006 | Nakamura et al. |

FOREIGN PATENT DOCUMENTS

| | | |
|---|---|---|
| JP | 3-218769 A | 9/1991 |
| JP | 4-002341 A | 1/1992 |
| JP | 4-054966 A | 2/1992 |
| JP | 6-125978 A | 5/1994 |
| JP | 6-154257 A | 6/1994 |
| JP | 7-047115 A | 2/1995 |
| JP | 9-51940 A | 2/1997 |
| JP | 11-043799 A | 2/1999 |
| JP | 2000-210313 A | 8/2000 |
| JP | 2002-248163 A | 9/2002 |
| JP | 2003-235954 A | 8/2003 |
| JP | 2005-533552 A | 11/2005 |
| WO | WO 03/049781 A1 | 6/2003 |
| WO | WO 2004008984 A1 * | 1/2004 |
| WO | WO 2004/062705 A1 | 7/2004 |

OTHER PUBLICATIONS

Extended European Search Report issued in corresponding European Application No. 06 83 4225 dated Oct. 21, 2010.
Atsuo Ito et al., In vitro biocompatibility, mechanical properties, and corrosion resistance of Ti-Zr-Nb-Ta-Pd and Ti-Sn-Nb-Ta-Pd alloys, Journal of Biomedical Materials Research, vol. 29, 893-900 (1995).
Larsson, C. et al., Bone response to surface-modified titanium implants: studies on the early tissue response to machined and electropolished implants with different oxide thicknesses, Biomaterials, 1996, vol. 17, pp. 605-616, Table 1, Results.
Wang, Xiao-Xiang Wang et al., "A comparative study of in vitro apatite deposition on heat-, H202-, and NaOH-treated titanium surfaces", Journal of Biomedical Materials Research, John Wiley & Sons, Inc., Periodicals, Inc., 2001, vol. 54, pp. 172-178.
Masao Yoshinari, "Implant Zairyo to sono Hyomen Sono 3. Implant Hyomen to Seitai" ("Inplant Materials, Implant Surfaces and Interface Processes Part 3.Implant surfaces and interface processes"), Shika Gakuho, 2003, pp. 565-572, vol. 13-No. 7, Department of Dental Materials Science, Tokyo Dental College.

* cited by examiner

*Primary Examiner* — Kriellion Sanders
(74) *Attorney, Agent, or Firm* — Buchanan Ingersoll & Rooney PC

(57) ABSTRACT

By forming a bone-compatible implant wherein a groove or hole has been formed in the surface of a base material made of titanium metal or a titanium alloy at its joint with a bone tissue and the groove or hole has on the inner surface thereof an oxide film formed by heating in an oxygen-containing atmosphere, apatite is allowed to deposit on the inner surface of the groove or hole easily. Thus, an implant is provided which can be attached to a bone within a relatively short period of time even without resorting to bone cement.

9 Claims, 2 Drawing Sheets

[Fig. 1]
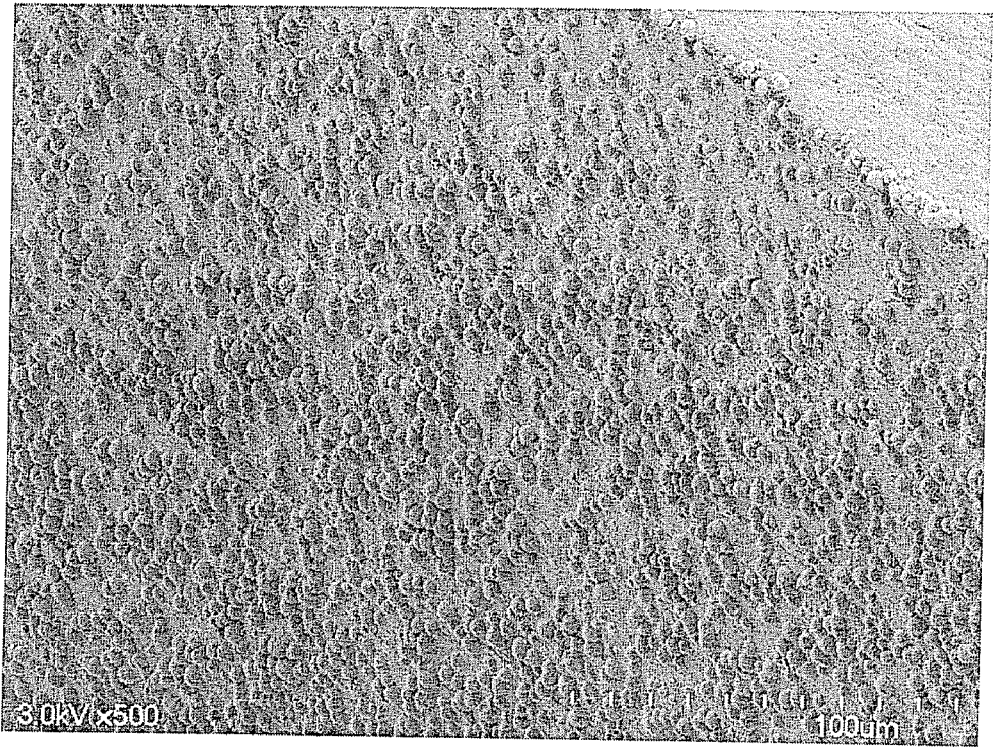
[Fig. 2]
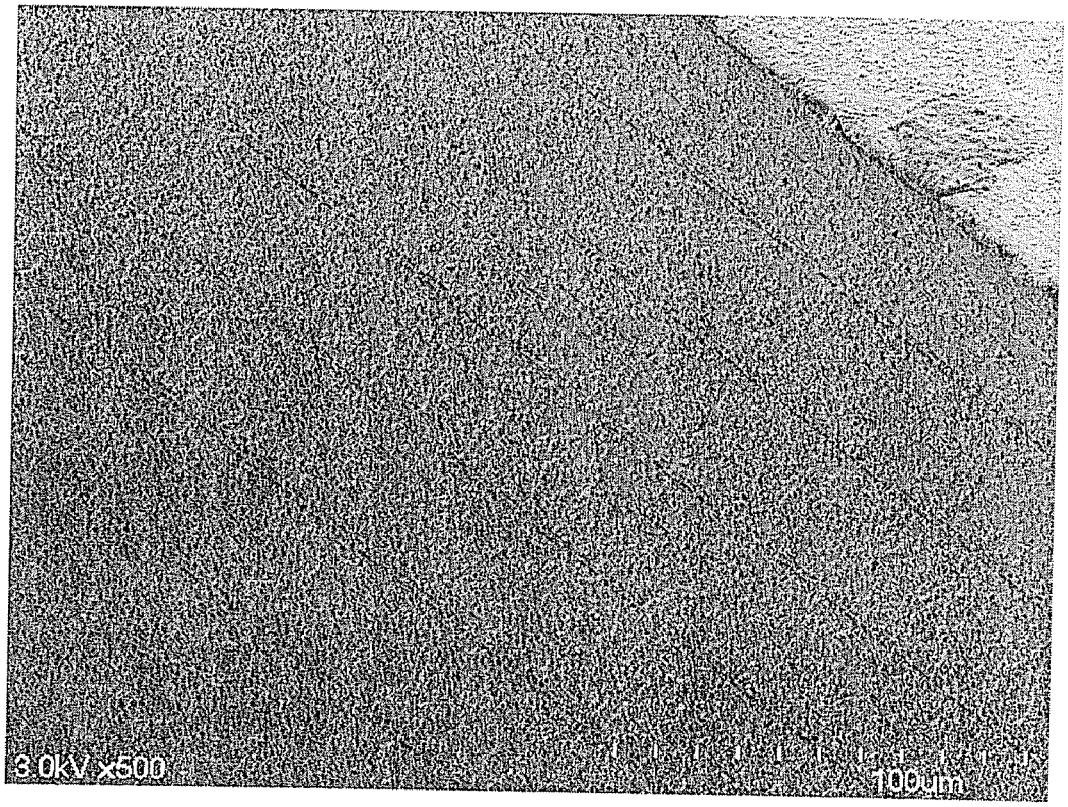

[Fig. 3]
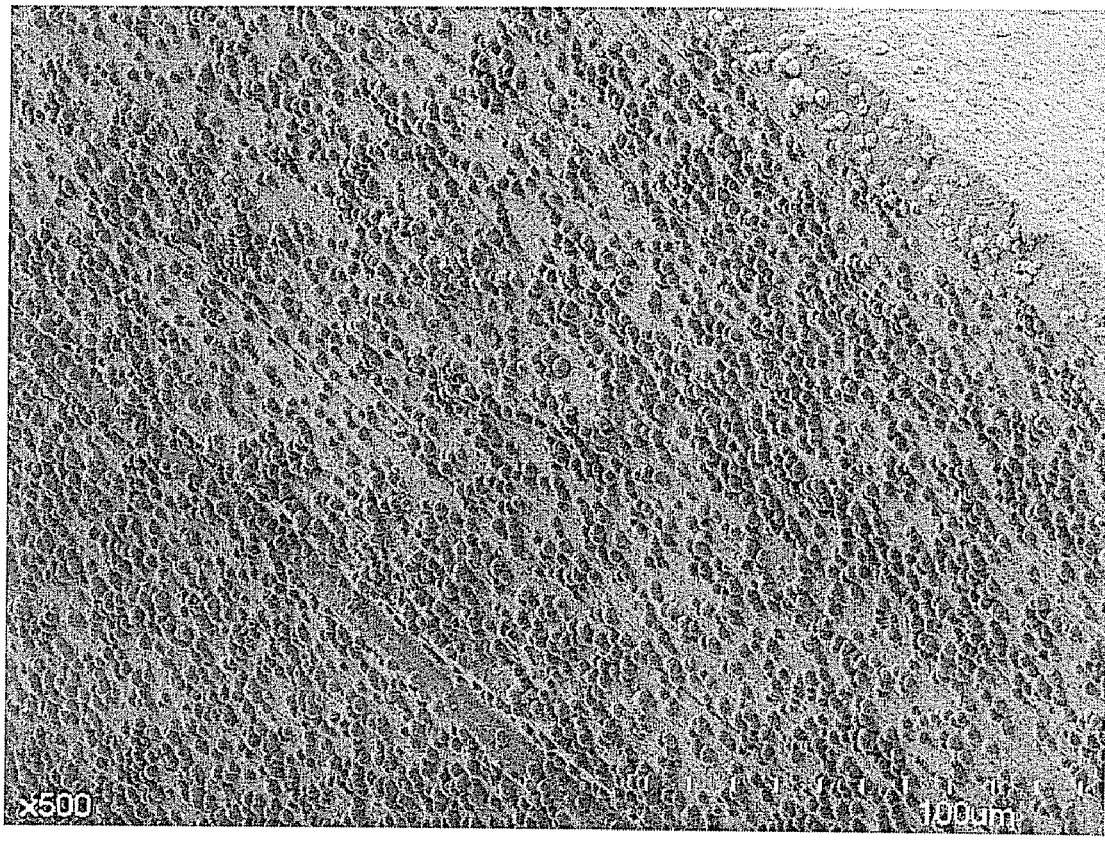

BONE-COMPATIBLE IMPLANT AND METHOD OF PRODUCING THE SAME

TECHNICAL FIELD

The present invention relates to an implant excellent in bone compatibility, which is made of titanium metal or a titanium alloy. The invention also relates to a method for producing such an implant.

BACKGROUND ART

In recent years, metal implants have increasingly been used widely in the fields of orthopedics and dentistry, such as artificial bones and artificial tooth roots. For example, when the function of a joint has been lost due to arthrosis deformans or rheumatoid arthritis, medical treatment for regaining the function by exchange to an artificial joint has become general.

As the method for fixing artificial joints to bones, two main types of methods are presently used. One is a technique of filling an adhesive called bone cement into a gap between a bone and an artificial joint to fix them. Since bone cement hardens during the operation, it becomes possible to start rehabilitation early after the operation. However, its use tends to decrease year by year because the risk of causing a shock disease or a blood pressure decline due to excessive compression to the bone marrow during the filling of bone cement has been reported. Another method is a fixing method called cementless fixation, which uses no bone cement. One example is a method of fixing by a mechanical anchoring effect caused by intrusion of a surrounding bone into a porous part formed in the surface of an artificial joint. Since this method can avoid the risk caused by use of bone cement, the cases using the method are increasing rapidly. However, since the time needed for an artificial joint to be fixed to a bone depends on the rate of growth of patient's bone, the patient is required to take a long rest.

In order to shorten the resting period when the aforementioned cementless fixation is adopted, some methods for imparting osteoconductive property to artificial joints have heretofore been investigated. One of them is a method in which osteoconductive property is imparted to the surface of an artificial joint by spraying hydroxyapatite, which is a bone-like component, at high temperatures, and it has already been in practical use. It, however, is supposed that this method has problems that large-scaled equipment for spraying is required, that apatite to be sprayed may be degraded due to exposure to high temperature, and that an apatite layer formed may exfoliate.

Patent document 1 discloses a bone substitutive material provided with specifically sized ruggedness and an alkali titanate layer on a bonding surface to a body tissue, which is a surface of a base material made of titanium or titanium alloy. It is disclosed that the bone substitutive material exhibits improved apatite-forming ability by having an alkali titanate layer on a base material surface and that a strong fixing force to a living bone by an anchoring effect due to the ruggedness can be obtained. As examples of the method for forming the ruggedness, sandblast treatment, and a method of spraying powder are provided. The aforementioned alkali titanate layer is formed by forming a layer of hydrated gel of sodium titanate by immersing a base material in an aqueous sodium hydroxide solution, followed by calcination. Although it is conceivable that the surface layer formed by this method is composed of a metal oxide layer containing titanium and sodium, it is not easy to completely confirm safety of such novel materials to living bodies.

Patent document 2 discloses an osteoconductive biomaterial comprising a metal base material containing titanium and a metal oxide layer formed on a surface of the metal base material, wherein at least a surface of the metal oxide layer has a chemical species composed of TiOH. The osteoconductive biomaterial having such a chemical species on its surface is formed by hydrothermally treating, under conditions including a temperature of 100° C. or higher and a pressure of 0.1 MPa or higher, a titanium oxide layer obtained by thermally treating a metal base material containing titanium at a temperature of 1000° C. or lower. At this time, the preferable thickness of the metal oxide layer formed by the thermal treatment is about 3 to about 10 µm. By adopting such a constitution, it is possible to provide a biomaterial with good osteoconductive property. For example, in Example 1 of Patent document 2, it is disclosed that a sample which had been obtained by forming a metal oxide layer of about 5 µm in a thickness by thermally treating a Ti-29Nb-13Ta-4.6Zr alloy at 800° C. for 1 hour, immersing the resultant in a phosphate buffer, and hydrothermally treating it under conditions of 120° C. and 0.2 MPa generated apatite crystals in a simulated body fluid. On the other hand, Comparative Example 2 of Patent document 2 discloses that no apatite crystals can be formed by only forming a metal oxide layer without conducting the aforementioned hydrothermal treatment. Moreover, Patent document 2 has no particular description concerning the shape of the surface of a metallic base material.

Non-patent document 1 discloses the result of the observation of apatite forming conditions by immersing, in a simulated body fluid, a titanium metal flat plate sample on the surface of which an oxide film had been formed by heat treatment in the air at 400° C. for 1 hour. In the experiment, the container containing the simulated body fluid was a polystyrene container having an upwardly curved bottom surface and the flat plate sample was immersed therein in such a way that the sample was placed on the curved bottom. Then, no apatite was formed on the upper surface of the sample, but formation of apatite only on the under surface (the side which comes into contact with the bottom of a container) was observed. Since the under surface of the sample was in contact with the curved surface of the container, the gap depended on the location, but in general apatite was easily formed at places where there was a gap of about 100 µm. However, the reason why apatite is formed at such places is not described. Moreover, non-patent document 1 has no particular description concerning the shape of the surface of a metallic base material.

Patent document 1: JP-A 2000-210313
Patent document 2: JP-A 2003-235954
Non-patent document 1: Xiao-Xiang Wang et al., three others, "A comparative study of in vitro apatite deposition on heat-, H2O2-, and NaOH-treated titanium", Journal of Biomedical Materials Research, John Wiley & Sons, Inc., Periodicals, Inc., 2001, vol. 54, pp. 172-178

DISCLOSURE OF THE INVENTION

Problem to be Solved by the Invention

The present invention was made in order to solve the problems mentioned above. An object of the present invention is to provide an implant excellent in bone compatibility and safety without using any special materials. Another object is to provide a method suitable for producing such an implant.

Means for Solving the Problem

The foregoing problems can be solved by providing a bone-compatible implant wherein a groove or hole is formed in the surface of a base material made of titanium metal or a titanium alloy at its joint with a bone tissue and the groove or hole has an oxide skin on the inner surface thereof. When the present inventors formed a groove in the surface of a base material made of titanium metal or a titanium alloy and then formed an oxide film on the overall surface, followed by immersion into in a simulated body fluid, they surprisingly found that an apatite was formed only inside the groove selectively. It seems that apatite is easy formed on the inner surface of a recess with an appropriate size. Therefore, by intentionally forming such a recess in the surface of an implant, it is possible to provide an implant excellent in bone compatibility.

In this embodiment, it is preferable that the oxide film be one formed by heating in an oxygen-containing atmosphere, and it is also preferable that the thickness thereof be 0.01 to 1 μm. Moreover, it is preferable that the width (W) of the groove or hole be 0.01 to 3 mm and that the depth (D) be 0.01 to 1 mm. It is also preferable that the ratio (D/W) of the depth (D) of the groove or hole to the width (W) of the groove or hole be 0.1 to 2. It is also preferable that the groove or hole has a cross sectional shape that is rectangle, trapezoid, U-shape or V-shape. It is preferable that the base material be substantially free from aluminum or vanadium. It is preferable that the base material be made of a titanium alloy which contains titanium with a content of 50% by weight or more and at least one metal selected from zirconium, tantalum, niobium and palladium with a combined content of 0.1 to 50% by weight.

The aforementioned problems can be solved by providing a method for producing a bone-compatible implant, wherein titanium metal or a titanium alloy is formed into a desired shape, then a groove or hole is formed in its surface at its joint with a bone tissue, and subsequently an oxide film is formed by heating the surface in an atmosphere containing oxygen. In this embodiment, it is preferable that the groove or hole be formed by at least one machining method selected from the group consisting of mechanical cutting, wire electric discharge machining, laser machining, water jet machining, press working, ultrasonic machining, and etching. It is also preferable to conduct polishing treatment after forming the groove or hole. It is also preferable that the heating temperature in the forming of the oxide film be 300 to 700° C. It is also preferable that treatment with water or water vapor at 80 to 300° C. be conducted after forming the oxide film. It is also preferable that immersion into an aqueous solution containing calcium ion or phosphate ion be conducted after forming the oxide film.

Effect of the Invention

The implant of the present invention is excellent in bone compatibility due to its susceptibility to formation of apatite on the surface thereof and therefore it is expected that it can be attached to a bone within a relatively short period of time even without resorting to bone cement. Moreover, it has high safety to living bodies because it has no coating of special materials. In addition, it can be produced relatively easily using ordinary production equipment.

BRIEF DESCRIPTION OF THE DRAWINGS

FIG. 1 is an electron micrograph obtained by observation of the condition of apatite particles formed in Example 1 on the inner surface of a groove having a width (W) of 500 μm and a depth (D) of 500 μm.

FIG. 2 is an electron micrograph obtained by observation of the condition of apatite particles formed on the inner surface of a groove treated with hot water in Example 2.

FIG. 3 is an electron micrograph obtained by observation of the condition of apatite particles formed on the inner surface of a groove in the Ti-15Zr-4Ta-4Nb-0.2Pd alloy sample heated at 500° C. in Example 3.

BEST MODE FOR CARRYING OUT THE INVENTION

The base material of the implant of the present invention is made of titanium metal (pure titanium) or a titanium alloy. When titanium metal is used as a base material, while the resulting implant is excellent in apatite-forming ability, it is occasionally insufficient in strength. It therefore is suitably used at regions where a large load is not applied, for example, artificial tooth roots. Titanium alloys containing metals other than titanium, some of which may have reduced apatite-forming ability, are preferably used as an artificial joint, an internal fixation material, an intramedullary nail, etc. at regions which receive so large a load that they are required to have strength because highly strong implants can be obtained therefrom.

The titanium alloy to be used in the present invention may be any alloy which contains titanium and is not particularly restricted. It, however, is preferable that the titanium content be 20% by weight, and it is more preferably 50% by weight or more. An alloy having a titanium content of 50% by weight or more is suitably used. Examples of the metal other than titanium to be incorporated in a titanium alloy include aluminum, vanadium, zirconium, tantalum, niobium, palladium and molybdenum. The most common titanium alloy among titanium alloys currently used for medical application is Ti-6Al-4V (a titanium alloy containing 6% by weight of aluminum, 4% by weight of vanadium, and titanium as the remainder). However, as shown in Examples described below, implants using this alloy as a base material had insufficient apatite-forming ability. On the basis of this fact, it is presumed that aluminum or vanadium in the alloys works to inhibit apatite formation. Therefore, from the point of view of apatite-forming ability, it is preferable that the base material to be used in the present invention be substantially free from aluminum or vanadium. In particular, because aluminum and vanadium are expected to develop toxicity to cells or metal allergy due to their elution, it is preferable that the base material be substantially free from them.

In order to obtain an implant excellent in strength, it is preferable to use not pure titanium but a titanium alloy. Specifically, a titanium alloy which contains titanium with a content of 50% by weight of more and at least one metal selected from zirconium, tantalum, niobium and palladium with a combined content of 0.1 to 50% by weight is preferably used. As shown also in Examples described below, it is shown that an implant using a titanium alloy composed of 15% by weight of zirconium, 4% by weight of tantalum, 4% by weight of niobium, 0.2% by weight of palladium and titanium as the remainder (Ti-15Zr-4Ta-4Nb-0.2Pd) as the base material is superior in apatite-forming ability in comparison to the case of using the aforementioned Ti-6Al-4V, and that the formation of apatite is not inhibited significantly even it contains zirconium, tantalum, niobium and palladium. Moreover, these metals are believed to generally have small adverse effects on living bodies. If the content of at least one metal selected from zirconium, tantalum, niobium and palladium is less than 0.1% by weight, there is a possibility that the strength may be insufficient in some applications. The content is more preferably 1% by weight or more (at this time, the titanium content is 99% by weight or less), even more preferably 5% by weight or more (the titanium content is 95% by weight or less), and particularly preferably 10% by weight or more (the titanium content is 90% by weight or less). On the other hand, if the content of at least one metal selected from zirconium, tantalum, niobium and palladium exceeds 50% by weight, the apatite-forming ability may deteriorate. The content is more preferably 40% by weight or less (the titanium content is 60% by weight or more), and it is even more preferably 30% by weight or less (the titanium content is 70% by weight or more).

In the implant of the present invention, a groove or hole has been formed in the surface of the base material at a joint with a bone tissue. The method for forming the groove or hole is not particularly restricted. The groove or hole may be formed directly by use of a template having a surface with such a shape, or alternatively formed in a surface of an object fabricated beforehand. Because implants having various dimensions or shapes are often needed, a method is preferred in which titanium metal or a titanium alloy is formed into a desired shape in advance and then a groove or hole is formed in its surface at a joint with a bone tissue. The forming method is not particularly restricted, and the formation can be performed by casting, forging, engraving, etc. In an artificial joint, for example, a groove or hole is formed in a portion which is to be inserted into a bone.

The method for forming a groove or hole in the surface of the base material at a joint with a bone tissue may be any method by which a recess with desired dimensions can be formed and is not particular restricted. The groove or hole can be formed in the surface of a shaped article by a method such as mechanical cutting, wire electric discharge machining, laser machining, water jet machining, press working, ultrasonic machining, and etching.

The shape and dimensions of the groove or hole thus formed are not particularly limited if apatite can be formed therein. It is permitted to render the cross sectional shape of a groove or hole rectangle, trapezoid, U-shape, V-shape, etc. A preferable cross sectional shape is adopted depending upon the machining method for forming the groove or hole. In particular, it is preferable to render it rectangle, trapezoid or U-shape in order to secure a wide interior space of the groove or hole. In order to have no weak part where stress concentrates, it is preferably a U-shape. Grooves may be formed almost in parallel to each other at predetermined intervals or may be formed so as to intersect with each other. When the grooves are formed so as to intersect with each other, parts other than the grooves remain in the form of islands. As to the hole, many holes are formed at proper intervals in the surface of the base material.

It is preferable that the width (W) of the groove or hole to be formed be 0.01 to 3 mm. When the width (W) is less than 0.01 mm, the interior space becomes so small that apatite might be formed insufficiently, and it will become difficult to machine it. If it is formed efficiently by a method such as mechanical cutting, wire electric discharge machining, laser machining, water jet machining, press working, ultrasonic machining and etching without adopting any special technique, such as chemical etching using lithography, it is practical that the width (W) be 0.1 mm or more. In view of both machinability and apatite formability, it is more preferable that the width (W) be 0.25 mm or more. Conversely, if the width (W) is greater than 3 mm, the interior space becomes so large that apatite might be formed insufficiently. The width (W) is preferably 1.5 mm or less, and even more preferably 0.8 mm or more. Here, the width (W) refers to the width of a portion where the surface of the base material has been cut in the implant as a product.

It is preferable that the depth (D) of the groove or hole to be formed be 0.01 to 1 mm. When the depth (D) is less than 0.01 mm, the interior space becomes so small that apatite might be formed insufficiently. The depth (D) is more preferably 0.1 mm or more, and even more preferably 0.25 mm or more. On the other hand, if the depth (D) is greater than 1 mm, the interior space becomes so large that apatite might be formed insufficiently and the mechanical strength of the implant might decrease. The depth (D) is more preferably 0.8 mm or less, and even more preferably 0.6 mm or less. Here, the depth (D) refers to the depth from the surface of the base material to the deepest portion of the groove or hole in the implant as a product.

It is preferable that the ratio (D/W) of the depth (D) of the groove or hole to the width (W) of the groove or hole be from 0.1 to 2. If the ratio (D/W) is less than 0.1, variation in distance between the bottom of the groove or hole and a bone tissue may result easily in installation in a bone, and areas where a space wide enough for forming apatite can not be secured may occur partially. This point is important because the surface of a bone does not necessarily meet the shape of the surface of an implant. The ratio (D/W) is more preferably 0.2 or more, and even more preferably 0.3 or more. If the ratio (D/W) is greater than 2, there are possibilities that not only the mechanical strength of the implant may decrease and also the machining operation for forming a groove or hole may become difficult. The ratio (D/W) is more preferably 1.5 or less, and even more preferably 1.2 or less.

Since the operation of forming a groove or hole may generate an edge or burr, it is preferable to conduct polishing treatment after forming a groove or hole. By this treatment, it is possible to remove an edge or burr generated at a part which will come into direct contact with a bone tissue. It thus smoothens the surface of a part where no groove or hole has been formed, and therefore it can render the surface of the part easier to come into contact with a bone tissue and it can attain safe installation. In this polishing operation, the interior part of the groove or hole may be either polished simultaneously or not. Conventionally, while there are many proposals of methods for roughening the surface of an implant, almost no methods of forming a groove or hole as well as polishing to smoothen the surface of a part where no groove or hole has been formed have been adopted. This is because while irregularities have heretofore been formed in the surface of an implant for the purpose of obtaining the mechanical anchoring effect conventionally, a recess is formed in the surface of an implant in the present invention for the purpose of securing a space wide enough for apatite formation. It is noted that while it is permitted to form an oxide film in advance and polish parts other than a groove or hole, it is usually preferable to form an oxide film after polishing.

A groove or hole is formed in such procedures, and then an oxide film is formed on the surface of the base material after, if necessary, polishing. Forming an oxide film in the inner surface of the groove or hole renders apatite easier to be formed inside the groove or hole. The method for forming the oxide film is not particularly restricted, and it may be formed by heating in an oxidizable atmosphere, or performing anodizing treatment, or immersing in a liquid containing an oxidizing agent. Among these, heating in an oxidizable atmosphere is preferred. Specifically, it is preferable to heat in an atmosphere containing oxygen, such as the room air. The operation of forming an oxide film by such a method is very easy and it usually has a high safety because a film to be formed is a material resulting from only the oxidation of the metal atoms contained in a base material.

It is preferable that a heating temperature in forming the oxide film be 300 to 700° C. If the heating temperature is lower than 300° C., an oxide film will be formed insufficiently, and therefore, there is a possibility that the apatite-forming ability may deteriorate. The heating temperature is more preferably 350° C. or higher. When a titanium alloy is used, a temperature required for forming an oxide film capable of forming apatite is higher than that in use of pure titanium. It, therefore, is preferable that the heating temperature be 400° C. or higher. On the other hand, if the heating temperature exceeds 700° C., there is a possibility that mechanical strength of the implant may deteriorate due to occurrence of change in the crystal structure of the titanium metal or titanium alloy of the base material. The heating temperature is more preferably 600° C. or lower, and even more preferably 550° C. or lower. While a heating time is determined properly depending upon the relationship with a heating temperature, it is usually from about 5 minutes to about 24 hours.

It is preferable that the thickness of an oxide film to be formed in such a manner be 0.01 to 1 μm. If the thickness of the oxide film is less than 0.01 μm, there is a possibility that the apatite-forming ability may deteriorate. The thickness of the oxide film is more preferably 0.05 μm or more, and even more preferably 0.1 μm or more. On the other hand, if the thickness of the oxide film is greater than 1 μm, it is feared that the film would exfoliate. The thickness of the oxide film is more preferably 0.7 μm or less, and even more preferably 0.5 μm or less.

It is also preferable to treat the oxide film after the formation thereof with water or water vapor at 80 to 300° C. By performing such treatment, the apatite-forming ability is improved in comparison to forming an oxide film by only heating in the air. It is possible to treat it using water of 80 to 100° C. under a normal pressure. However, in order to obtain a sufficient effect, it is preferable to treat it under pressurized conditions using water or water vapor of 100° C. or higher, and more preferably of 120° C. or higher. On the other hand, when treatment is performed using water or water vapor above 300° C., the treating equipment will be a large scale. It is more preferably 200° C. or lower. The time of treating with water or water vapor is normally about 5 minutes to about 24 hours.

It is also preferable that immersion into an aqueous solution containing calcium ion and phosphate ion be conducted after forming the oxide film and then installation to a bone be carried out. This makes it possible to conduct installation to a bone after causing apatite particles or the precursor thereof to deposit beforehand on the inner surface of the groove or hole, and to establish attachment to a bone more rapidly. While it is preferable that a substance to be formed on the inner surface of the groove or hole be apatite particles in this case, an effect can be expected even if a precursor of such particles is formed. The aqueous solution containing a calcium ion and a phosphate ion to be used here may be any aqueous solution capable of depositing apatite particles or a precursor thereof and may contain other ingredients. For example, it may contain a sodium ion, a potassium ion, a magnesium ion, a chlorine ion, a carbonate ion, a sulfate ion, etc., which are contained in body fluid ingredients. The use of a simulated body fluid is particularly preferred. It is also permitted to conduct immersion into an aqueous solution containing a calcium ion and a phosphate ion after the formation of the oxide film and the subsequent treatment with water or water vapor.

The implant of the present invention produced in the aforementioned procedures can be used widely in orthopedics applications or dental applications because it is excellent in bone compatibility and safety without using no special materials. For example, it can be used suitably in applications such as artificial joints, artificial tooth roots, internal fixation devices and intramedullary nails. It is expected that it can be attached to a bone within a relatively short period of time even without using any bone cement.

EXAMPLES

The present invention will be described in more detail with reference to Examples.

Example 1

Influence of Groove Dimensions

In one side of a plate made of medical use grade titanium metal (pure metal) sized 12 mm×12 mm×5 mm, a groove with a rectangular cross section was formed from one edge to the other edge of the plate using an end mill. In one sample, grooves were formed while varying their width (W) as 200 μm, 500 μm, μm and 1000 μm with their depth (D) fixed at 200 μm. Three samples in each of which four grooves with a fixed depth (D) of 500 μm, 800 μm or 1000 μm, respectively, had been formed with four different widths (W) as mentioned above were also produced. Then, heat treatment was conducted in the air at 400° C. for 1 hour within a muffle furnace. All the samples after the heat treatment assumed bronze color. On the basis of this color, it was found that titanium oxide films with a thickness of about 0.12 to about 0.2 μm were formed.

A simulated body fluid having an inorganic ion concentration almost equal to those of the human body fluid was prepared. The ion concentrations were $Na^+$ 142.0 mM (millimole/liter), $K^+$ 5.0 mM, $Mg^{2+}$ 1.5 mM, $Ca^{2+}$ 2.5 mM, $Cl^-$ 147.8 mM, $HCO_3^-$ 4.2 mM, $HPO_4^{2-}$ 1.0 mM, and $SO_4^{2-}$ 0.5 mM. The pH at 36.5° C. was 7.4. Into a flat-bottomed, cylindrical polystyrene container having a diameter of 58 mm and a height of 21 mm, 30 mL of this simulated body fluid was charged. The samples obtained by heating after forming the grooves were immersed one by one after degreasing with acetone into the simulated body fluid with the grooved side down. Then, they were left at rest in a thermostatic bath at 36.5° C. for one week.

After one week, the samples were taken out from the simulated body fluid and the surfaces of the samples were observed with a scanning electron microscope. As a result, the situation where spherical apatite particles as large as about 3 to 5 μm had deposited on the inner surfaces of the grooves was observed. In all the samples, no formation of apatite particles was observed in the surfaces of the samples outside the grooves. Therefore, the formation of apatite on the inner surface of a groove is selective. The forming statuses are shown collectively in Table 1. At this time, the forming status was evaluated as grades A, B and C in decreasing order of the deposited amount on the inner surface of a groove and a sample in which no apatite was formed was evaluated as grade D. As a typical example, a photograph showing the forming situation of apatite particles when the width (W) was 500 μm and the depth (D) was 500 μm is shown in FIG. 1. The elemental analysis of the deposited matter revealed that it contained phosphorus element and calcium element. Taking into consideration the form of the deposited matter as well, it is expected to be a bone-like apatite which is the same type as those which deposit on the surface of other bioactive materials.

TABLE 1

| Width (W) (μm) | Depth (D) (μm) | (D/W) | Apatite formation status*1) |
|---|---|---|---|
| 200 | 200 | 1 | B |
|  | 500 | 2.5 | B |
|  | 800 | 4 | A |
|  | 1000 | 5 | A |
| 500 | 200 | 0.4 | B |
|  | 500 | 1 | A |
|  | 800 | 1.6 | A |
|  | 1000 | 2 | A |
| 800 | 200 | 0.25 | B |
|  | 500 | 0.625 | A |
|  | 800 | 1 | A |
|  | 1000 | 1.25 | A |
| 1000 | 200 | 0.2 | C |
|  | 500 | 0.5 | C |
|  | 800 | 0.8 | D |
|  | 1000 | 1 | D |

As seen from Table 1, as to the grooves having a width (W) of 1000 μm, no apatite was formed when the depth (D) was 800 μm or more, and apatite was formed in a small amount even when the depth (D) was 500 μm or less. This result showed that when the width (W) is excessively large and the cross sectional area of the groove is excessively large, the formation of apatite tends to be suppressed. On the other hand, as to the grooves having a width (W) of 800 μm or less, when the depth (D) was 200 μm, the amount of apatite formed was not large and, in particular, the forming density in the vicinity of the opening of the groove was low. As to the grooves with a width (W) of 200 μm, the amount of apatite formed was not large even when the depth (D) was 500 μm. These facts show that if a groove is excessively shallow or the cross sectional area of a groove is excessively small, the formation of apatite tends to be suppressed. That is, it has been found that the formation of apatite is promoted by forming a recess having dimensions within specific ranges.

Comparative Example 1

No Heat Treatment

A groove having a width (W) of 500 μm and a depth (D) of 500 μm was formed in one side of a plate of titanium metal (pure titanium) in the same method as Example 1. Then, a test of immersing a sample into a simulated body fluid as in Example 1 was performed without conducting heat treatment. As a result, no apatite formation on the inner surface of a groove was observed at all. No apatite formation was observed at all also on the sample surface outside the grooves.

Example 2

Influence of Hot Water Treatment

A groove having a width (W) of 500 μm and a depth (D) of 500 μm was formed in one side of a plate of titanium metal (pure titanium) in the same method as Example 1. Then, heat treatment was conducted in the air at 400° C. for 1 hour within a muffle furnace in the same manner as Example 1. The heat-treated sample was supplied to a pressure container containing distilled water, and was heated at 150° C. for 24 hours. The resulting sample was subjected to a test of immersing it into a simulated body fluid as in Example 1. As a result, the situation where spherical apatite particles as large as about 0.5 to 1 μm had deposited on the inner surface of the groove was observed. At this time, a small amount of spherical apatite particles with a size similar to the foregoing had been formed on the sample surface outside the groove as well. The amount of apatite particles formed within the groove is larger than that of the outside of the groove and, in a deep area, the inner surface was covered with apatite particles with almost no gaps. That is, it has been found that it is possible to cause apatite small in a particle size to deposit densely on the inner surface of a groove by treating with hot water.

Example 3

Use of Titanium Alloy

In Example 1, using plates of two kinds of titanium alloys, Ti-6Al-4V and Ti-15Zr-4Ta-4Nb-0.2Pd, the dimensions of which were the same as those in Example 1, instead of the plate of titanium metal (pure titanium), a groove having a width (W) of 500 μm and a depth (D) of 500 μm was formed in one side of each of the plates. For each of the alloys, two alloy samples provided with a groove were produced, and then a sample having been heat treated at 400° C. for 1 hour and the other sample having been heat treated at 500° C. for 1 hour were prepared. These total four samples were subjected to a test of immersing them into a simulated body fluid in the same manner as Example 1. As a result, for both the alloys, no apatite was formed on the samples heated to 400° C. As to Ti-6Al-4V, no apatite was formed even in the sample heated to 500° C. However, as to Ti-15Zr-4Ta-4Nb-0.2Pd, it was confirmed that apatite particles as large as about 3 to 5 μm were deposited on the inner surface of the groove in the sample heated to 500° C. At this time, spherical apatite particles with a size similar to the foregoing had been formed on the sample surface outside the groove as well, the amount thereof was very small in comparison to the inner surface of the groove. According to this result, it seems that titanium alloys are more difficult to form an oxide film than pure titanium and require higher temperatures for forming it. Moreover, while it was difficult to form apatite in the alloy containing aluminum and vanadium, the formation of apatite was observed in the alloy containing zirconium, tantalum, niobium and palladium, and therefore it was shown that the latter is more suitable as a base material of the implant of the present invention.

The invention claimed is:

1. A bone-compatible implant wherein a groove has been formed in a surface of a base material made of titanium metal or a titanium alloy at a joint with a bone tissue and the groove has an oxide film on an inner surface thereof;
   wherein the base material is substantially free from aluminum or vanadium,
   wherein the groove has a width (W) of 0.25 to 0.8 mm and a depth (D) of 0.25 to 1 mm, and a ratio (D/W) of the depth (D) to the width (W) is from 0.1 to 2, and
   wherein the oxide film has a thickness of 0.01 to 1 μm and has been formed by heating in an oxygen-containing atmosphere.

2. The bone-compatible implant according to claim 1, wherein the groove has a cross sectional shape which is rectangle, trapezoid, U-shape or V-shape.

3. The bone-compatible implant according to claim 1, wherein the base material is made of a titanium alloy which contains titanium with a content of 50% by weight or more and at least one metal selected from zirconium, tantalum, niobium and palladium with a combined content of 0.1 to 50% by weight.

4. A method for producing the bone-compatible implant according to claim 1, wherein titanium metal or a titanium alloy is formed into a desired shape, then the groove is formed in the surface of the titanium metal or titanium alloy at the joint with a bone tissue, and subsequently the oxide film is formed on the surface by heating the surface in an oxygen-containing atmosphere.

5. The method for producing a bone-compatible implant according to claim 4, wherein the groove is formed by at least one machining method selected from the group consisting of mechanical cutting, wire electric discharge machining, laser machining, water jet machining, press working, ultrasonic machining, and etching.

6. The method for producing a bone-compatible implant according to claim 4, wherein polishing treatment of the surface is conducted after forming of the groove.

7. The method for producing a bone-compatible implant according to claim 4, wherein the heating temperature in the forming of the oxide film is 300 to 700° C.

8. The method for producing a bone-compatible implant according to claim 4, wherein treatment of the oxide film with water or water vapor at 80 to 300° C. is conducted after the forming of the oxide film.

9. The method for producing a bone-compatible implant according to claim 4, wherein immersion of the oxide film into an aqueous solution containing a calcium ion and a phosphate ion is conducted after the forming of the oxide film.

* * * * *